United States Patent
Liu et al.

(10) Patent No.: US 10,858,332 B1
(45) Date of Patent: *Dec. 8, 2020

(54) METHOD FOR PURIFYING CRUDE 2,5-FURANDICARBOXYLIC ACID COMPOSITION

(71) Applicant: FAR EASTERN NEW CENTURY CORPORATION, Taipei (TW)

(72) Inventors: Shu-Wei Liu, Taipei (TW); Ruey-Fen Liao, Taipei (TW); Xin-An Lu, Taipei (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/736,046

(22) Filed: Jan. 7, 2020

(30) Foreign Application Priority Data

Jul. 2, 2019 (TW) .............................. 108123216 A

(51) Int. Cl.
*C07D 307/68* (2006.01)
*B01D 11/02* (2006.01)

(52) U.S. Cl.
CPC ........ *C07D 307/68* (2013.01); *B01D 11/0288* (2013.01)

(58) Field of Classification Search
CPC .................................................. C07D 307/68
USPC ........................................................ 549/487
See application file for complete search history.

(56) References Cited

U.S. PATENT DOCUMENTS

| 9,896,425 | B2 * | 2/2018 | Singh | ................... | C07D 307/68 |
| 2012/0302768 | A1 * | 11/2012 | Janka | ................... | C07D 307/68 |
| | | | | | 549/485 |

* cited by examiner

*Primary Examiner* — Patricia L Morris
(74) *Attorney, Agent, or Firm* — MLO, a professional corp.

(57) ABSTRACT

A method for purifying a crude 2,5-furandicarboxylic acid composition including 2,5-furandicarboxylic acid and 5-formylfuran-2-carboxylic acid is disclosed. The method includes the steps of: (a) subjecting the crude 2,5-furandicarboxylic acid composition to complete dissolution in a solvent solution to obtain a mixture, the solvent solution including an organic solvent and water; (b) subjecting 5-formylfuran-2-carboxylic acid in the mixture to an addition reaction with sodium hydrogen sulfite to obtain an addition product; and (c) subjecting 2,5-furandicarboxylic acid to precipitation after step (b) to obtain purified 2,5-furandicarboxylic acid.

9 Claims, No Drawings

METHOD FOR PURIFYING CRUDE 2,5-FURANDICARBOXYLIC ACID COMPOSITION

CROSS-REFERENCE TO RELATED APPLICATION

This application claims priority of Taiwanese Patent Application No. 108123216, filed on Jul. 2, 2019.

FIELD

The present disclosure relates to a method for purifying a crude 2,5-furandicarboxylic acid composition, and more particularly to a method for purifying a crude 2,5-furandicarboxylic acid composition that includes 5-formylfuran-2-carboxylic acid.

BACKGROUND 2,5-furandicarboxyclic acid (FDCA) is a compound that can be produced from biomass without requiring chemical refinement, and thus its production is regarded as adhering to the concepts of green chemistry. FDCA can be used as a bio-based alternative to terephthalic acid, which is a raw material in the production of polyethylene terephthalate (PET). In fact, as compared with PET, polyethylene furanoate (PEF), which is a chemical analogue of PET and is produced from FDCA, exhibits even intrinsically higher gas barrier properties for oxygen, water vapor, carbon dioxide, etc.

Conventionally, the industrial method for synthesizing FDCA which adheres to the concepts of green chemistry, involves catalytic oxidation of furan derivatives (e.g., 5-hydroxymethylfurfural (HMF), 5-(alkoxymethyl)furfural (RMF), etc.) that are produced from the dehydration of saccharides. However, the thus obtained crude FDCA (cFDCA) usually contains impurities of furan derivatives, particularly monocarboxylic acid species such as 5-formylfuran-2-carboxylic acid (FFCA). If the cFDCA is not further purified, the impurities of furan derivatives contained therein may cause an undesirable effect of terminating the chain growth of a polymer, resulting in a low polymer viscosity of the thus obtained PEF which may in turn affect the thermoplastic properties thereof.

U.S. Pat. No. 8,969,404 B2 discloses a process for purifying crude FDCA composition by subjecting FFCA contained therein to hydrogenation reaction so as to form other types of water-soluble furan derivatives, which are then separated from water-insoluble FDCA. However, requirements of a high hydrogen partial pressure and an expensive catalyst such as palladium on carbon (Pd/C), etc. in the hydrogenation reaction incur a high processing cost.

SUMMARY

Therefore, an object of the present disclosure is to provide a method for purifying a crude 2,5-furandicarboxyclic acid composition which can alleviate at least one of the drawbacks of the prior art.

According to the present disclosure, the crude 2,5-furandicarboxylic acid composition includes 2,5-furandicarboxylicacid andfuran derivatives which contain 5-formylfuran-2-carboxylic acid. The method includes the steps of:

(a) subjecting the crude 2,5-furandicarboxylic acid composition to complete dissolution in a solvent solution so as to obtain a mixture, the solvent solution includes an organic solvent and water;

(b) subjecting the 5-formylfuran-2-carboxylic acid in the mixture to an addition reaction with sodium hydrogen sulfite so as to obtain an addition product; and (c) after step (b), subjecting the 2,5-furandicarboxylic acid to precipitation so as to obtain purified 2,5-furandicarboxylic acid.

DETAILED DESCRIPTION

According to the present disclosure, a method for purifying a crude 2,5-furandicarboxylic acid composition includes the following steps (a) to (c). The crude 2,5-furandicarboxylic acid composition includes 2,5-furandicarboxylic acid and furan derivatives which contain 5-formylfuran-2-carboxylic acid.

In step (a), the crude 2,5-furandicarboxylic acid composition is completely dissolved in a solvent solution that contains an organic solvent and water, so as to obtain a mixture.

In step (b), the 5-formylfuran-2-carboxylic acid in the mixture is subjected to an addition reaction with sodium hydrogen sulfite, so as to obtain an addition product.

In step (c), the 2,5-furandicarboxylic acid is subjected to precipitation so as to obtain purified 2,5-furandicarboxylic acid.

In certain embodiments, the organic solvent is water-miscible. Examples of the organic solvent may include, but are not limited to, alcohol, amide, lactam, ether, sulfoxide, and combinations thereof. Examples of the alcohol may include, but are not limited to, methanol, ethanol, isopropanol, and combinations thereof. Examples of the amide may include, but are not limited to, dimethylformamide, dimethylacetamide, and the combination thereof. An example of the lactam may include, but is not limited to, N-methylpyrrolidone. Examples of the ether may include, but are not limited to, tetrahydrofuran, diethyl ether, and the combination thereof. An example of the sulfoxide may include, but is not limited to, dimethyl sulfoxide.

In certain embodiments, in the solvent solution, a weight ratio of the organic solvent to the water ranges from 1.5:1 to 6:1.

In certain embodiments, in step (b), the addition reaction is conducted at a first temperature ranging from 40° C. to 120° C.

In certain embodiments, in step (c), the precipitation is conducted at a second temperature ranging from 0° C. to 30° C.

In certain embodiments, the method further includes, before step (c), a step (c') of adding water to the additional product so as to dissolve the sodium hydrogen sulfite that remains unreacted after step (b).

According to this disclosure, the method may further include, after step (c), a step (d) of removing the addition product. In certain embodiments, step (d) is conducted by collecting the purified FDCA obtained in step (c) by filtration, followed by drying the thus collected purified FDCA. The present disclosure will be further described by way of the following examples. However, it should be understood that the following examples are intended solely for the purpose of illustration and should not be construed as limiting the present disclosure in practice.

EXAMPLES

Example 1 (E1)

First, 24 g of a solvent solution (a weight ratio of methanol to water was 5:3) was added to 1.0 g of a crude 2,5-furandicarboxylic acid (cFDCA) composition that includes 2,5-furandicarboxylic acid (FDCA) and furan derivatives (i.e., approximately 7500 ppm of 5-formylfuran-2-carboxylic acid (FFCA)) in a container to completely dissolve the cFDCA composition so as to obtain a mixture. Next, 0.3 g of sodium hydrogen sulfite (NaHSO$_3$) was added to the mixture, and the container was sealed. Then, the thus sealed container was heated to a first temperature of 90° C., which was maintained for 30 minutes, allowing the NaHSO$_3$ to react with the FFCA in the mixture, so as to obtain an addition product, which may contain unreacted NaHSO$_3$. After that, an appropriate amount of water was added to the addition product to dissolve the unreacted NaHSO$_3$. Subsequently, the container was cooled to a second temperature of 0° C., which was maintained for 30 minutes, so as to precipitate FDCA in the mixture. The mixture was subjected to suction filtration so as to remove liquid portion thereof which contains the addition product, and then the precipitated FDCA thus collected was dried to obtain a solid product containing purified FDCA.

Examples 2 and 3 (E2 and E3)

The methods of E2 and E3 were similar in procedure to E1, except that the amount of NaHSO$_3$ used in E2 and E3 were 0.6 g and 0.9 g, respectively.

Examples 4 and 5 (E4 and E5)

The methods of E4 and E5 were similar in procedure to E1, except that, in the solvent solution, the weight ratio of methanol to water in E4 and E5 were 5:2 and 15:1, respectively.

Example 6 (E6)

First, 9.3 g of a solvent solution (a weight ratio of dimethylacetamide to water was 2:1) was added to 1.0 g of the cFDCA composition as described in E1 in a container to completely dissolve the cFDCA composition so as to obtain a mixture. Next, 0.3 g of NaHSO$_3$ was added to the mixture, and the container was sealed. Then, the thus sealed container was heated to a first temperature of 50° C., which was maintained for 30 minutes, allowing the NaHSO$_3$ to react with the FFCA in the mixture, so as to obtain an addition product, which contains unreacted NaHSO$_3$. After that, an appropriate amount of water was added to the addition product to dissolve the unreacted NaHSO$_3$. Subsequently, the container was cooled to a second temperature of 0° C., which was maintained for 30 minutes, so as to precipitate FDCA. The mixture was subjected to suction filtration so as to remove liquid portion thereof which contains the addition product, and then the precipitated FDCA thus collected was dried to obtain a solid product containing purified FDCA.

Example 7 (E7)

The method of E7 was similar in procedure to E6, except that the amount of NaHSO$_3$ was 0.6 g.

Example 8 (E8)

The method of E8 was similar in procedure to E6, except that the amount of the solvent solution was 7.3 g, and the weight ratio of dimethylacetamide to water in the solvent solution was 6:1.

Comparative Example 1 (CE1)

The method of CE1 was similar in procedure to E1, except that NaHSO$_3$ was omitted.

Comparative Example 2 (CE2)

The method of CE2 was similar in procedure to E2, except that the solvent solution was replaced with methanol.

Comparative Example 3 (CE3)

The method of CE3 was similar in procedure to E2, except that the solvent solution was replaced with water.
Determination of FFCA Removal Percentage and FDCA Percentage Purity In order to determine FFCA and FDCA contents, the cFDCA composition before purification and each of the solid products obtained by the methods of E1 to E8 and CE1 to CE3 were respectively dissolved in methanol and then subjected to high-performance liquid chromatography analysis (column type: ICE-COREGEL87H3 from Transgenomic, Inc.; mobile phase: 0.2% phosphoric acid solution). FFCA removal percentage was calculated using the formula: [1−(A/B)]×100%, in which A represents the FFCA content (ppm) in the purified solid product and B represents the FFCA content (ppm) in the cFDCA composition. FDCA percentage purity was calculated using the formula: (C/D)×100%, in which C represents the weight of FDCA in the purified solid product, and D represents the total weight of the purified solid product. The results were shown in Table 1 below.

TABLE 1

|  | FFCA removal percentage (%) | FDCA percentage purity (%) |
| --- | --- | --- |
| E1 | 90.0 | 99.8 |
| E2 | 96.8 | 99.9 |
| E3 | 97.3 | 99.8 |
| E4 | 82.9 | 99.8 |
| E5 | 76.0 | 99.6 |
| E6 | 97.7 | 99.9 |
| E7 | 98.0 | 99.9 |
| E8 | 97.6 | 99.9 |
| CE1 | 48.2 | 99.4 |
| CE2 | 64.9 | 99.5 |
| CE3 | 41.2 | 99.4 |

As shown in Table 1, the FFCA removal percentage in each of E1 to E8 is higher than 76', and the FDCA percentage purity thereof is higher than 99.6%, indicating that FFCA was effectively removed from the cFDCA composition, thereby obtaining a highly purified FDCA. In contrast, the FFCA removal percentage in each of CE1 to CE3 is lower than 64.9%, and the FDCA percentage purity thereof is lower than 99.5%, indicating that FFCA cannot be effectively removed from the cFDCA composition, and thus, a highly purified FDCA was not obtainable.

In summary, by virtue of reacting the furan derivatives (such as FFCA) of the cFDCA composition with NaHSO$_3$ in a solvent solution which includes an organic solvent and water, the method of the present disclosure is capable of effectively removing the furan derivatives from the cFDCA composition, thereby obtaining FDCA with high purity.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the present disclosure and aiding in the understanding of various inventive aspects, and that one or more features or specific details from one embodiment may be practiced together with one or more features or specific details from another embodiment, where appropriate, in the practice of the disclosure.

While the present disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for purifying a crude 2,5-furandicarboxylic acid composition, which includes 2,5-furandicarboxylic acid and 5-formylfuran-2-carboxylic acid, the method comprising the steps of:
    (a) subjecting the crude 2,5-furandicarboxylic acid composition to complete dissolution in a solvent solution so as to obtain a mixture, the solvent solution including an organic solvent and water, the organic solvent being selected from the group consisting of alcohol, amide, lactam, ether, sulfoxide, and combinations thereof;
    (b) subjecting the 5-formylfuran-2-carboxylic acid in the mixture to an addition reaction with sodium hydrogen sulfite, so as to obtain an addition product; and
    (c) after step (b), subjecting the 2,5-furandicarboxylic acid to precipitation so as to obtain purified 2,5-furandicarboxylic acid.

2. The method as claimed in claim 1, wherein the organic solvent is alcohol selected from the group consisting of methanol, ethanol, isopropanol, and combinations thereof.

3. The method as claimed in claim 1, wherein the organic solvent is amide selected from the group consisting of dimethylformamide, dimethylacetamide, and the combination thereof.

4. The method as claimed in claim 1, wherein the organic solvent is lactam, and the lactam is N-methylpyrrolidone.

5. The method as claimed in claim 1, wherein in the solvent solution, a weight ratio of the organic solvent to water ranges from 1.5:1 to 6:1.

6. The method as claimed in claim 1, wherein in step (b), the addition reaction is conducted at a first temperature ranging from 40° C. to 120° C.

7. The method as claimed in claim 1, wherein in step (c), the precipitation is conducted at a second temperature ranging from 0° C. to 30° C.

8. The method as claimed in claim 1, further comprising, before step (c), a step (c') of adding water to the addition product so as to dissolve the sodium hydrogen sulfite that remains unreacted after step (b).

9. The method as claimed in claim 1, further comprising, after step (c), a step (d) of removing the addition product.

* * * * *